US008403996B2

(12) United States Patent
Brekke et al.

(10) Patent No.: US 8,403,996 B2
(45) Date of Patent: *Mar. 26, 2013

(54) DEVICE FOR REGENERATION OF ARTICULAR CARTILAGE AND OTHER TISSUE

(75) Inventors: John H. Brekke, Duluth, MN (US); Gino Bradica, Claremont, NH (US); Scott M. Goldman, Paoli, PA (US)

(73) Assignee: Kensey Nash Corporation, Exton, PA (US)

( * ) Notice: Subject to any disclaimer, the term of this patent is extended or adjusted under 35 U.S.C. 154(b) by 1822 days.

This patent is subject to a terminal disclaimer.

(21) Appl. No.: 11/564,788

(22) Filed: Nov. 29, 2006

(65) Prior Publication Data

US 2011/0112655 A1    May 12, 2011

Related U.S. Application Data

(60) Continuation of application No. 10/830,267, filed on Apr. 21, 2004, now Pat. No. 7,963,997, which is a continuation of application No. 10/199,961, filed on Jul. 19, 2002, now abandoned, which is a continuation-in-part of application No. 09/909,027, (Continued)

(51) Int. Cl.
A61F 2/02 (2006.01)
(52) U.S. Cl. .................................. 623/23.72
(58) Field of Classification Search .............. 606/115, 606/213; 523/113–115; 623/13.17, 13.18, 623/14.12, 23.72–23.76, 23.61, 23.63
See application file for complete search history.

(56) References Cited

U.S. PATENT DOCUMENTS

| | | | |
|---|---|---|---|
| 3,948,254 A | 4/1976 | Zaffaroni | |
| 4,186,448 A | 2/1980 | Brekke | |
| 4,282,351 A | 8/1981 | Muzzarelli | |
| 4,485,097 A * | 11/1984 | Bell | 424/549 |
| 4,520,821 A * | 6/1985 | Schmidt et al. | 606/151 |
| 4,642,120 A | 2/1987 | Nevo et al. | |
| 4,708,951 A | 11/1987 | Inagaki et al. | |
| 4,783,335 A | 11/1988 | Lipshitz | |
| 4,853,225 A | 8/1989 | Wahlig et al. | |
| 5,041,138 A | 8/1991 | Vacanti et al. | |
| 5,071,656 A | 12/1991 | Lee et al. | |
| 5,110,604 A | 5/1992 | Chu et al. | |
| 5,133,755 A | 7/1992 | Brekke | |
| 5,152,791 A | 10/1992 | Hakamatsuka et al. | |
| 5,166,187 A | 11/1992 | Collombel et al. | |
| 5,268,178 A | 12/1993 | Calhoun et al. | |
| 5,294,446 A | 3/1994 | Schlameus et al. | |
| 5,306,311 A * | 4/1994 | Stone et al. | 623/14.12 |
| 5,356,429 A | 10/1994 | Seare | |
| 5,376,376 A | 12/1994 | Li | |
| 5,387,419 A | 2/1995 | Levy et al. | |
| 5,447,725 A | 9/1995 | Damani et al. | |
| 5,490,962 A | 2/1996 | Cima et al. | |
| 5,508,036 A | 4/1996 | Bakker et al. | |
| 5,512,600 A | 4/1996 | Mikos et al. | |
| 5,514,378 A | 5/1996 | Mikos et al. | |
| 5,632,727 A | 5/1997 | Tipton et al. | |
| 5,686,091 A | 11/1997 | Leong et al. | |
| 5,711,960 A | 1/1998 | Shikinami | |
| 5,723,331 A | 3/1998 | Tubo et al. | |
| 5,759,830 A | 6/1998 | Vacanti et al. | |
| 5,830,493 A | 11/1998 | Yokota | |
| 5,876,452 A | 3/1999 | Athanasiou et al. | |
| 5,972,027 A | 10/1999 | Johnson | |
| 5,981,825 A | 11/1999 | Brekke | |
| 6,013,853 A | 1/2000 | Athanasiou et al. | |
| 6,296,630 B1 | 10/2001 | Altman et al. | |
| 6,296,667 B1 * | 10/2001 | Johnson et al. | 623/23.61 |
| 6,306,169 B1 | 10/2001 | Lee et al. | |
| 6,350,226 B1 | 2/2002 | Fischell et al. | |
| 6,471,983 B1 | 10/2002 | Veeger et al. | |
| 6,471,993 B1 | 10/2002 | Shastri et al. | |
| 6,534,693 B2 | 3/2003 | Fischell et al. | |
| 6,635,049 B1 | 10/2003 | Robinson et al. | |
| 6,685,697 B1 | 2/2004 | Arenberg et al. | |
| 6,726,920 B1 | 4/2004 | Theeuwes et al. | |
| 6,726,923 B2 | 4/2004 | Iyer et al. | |
| 6,730,016 B1 | 5/2004 | Cox et al. | |
| 6,748,653 B2 | 6/2004 | Lindemans et al. | |
| 2002/0150622 A1 | 10/2002 | Philbrook et al. | |

(Continued)

FOREIGN PATENT DOCUMENTS

| | | |
|---|---|---|
| EP | 0369034 | 5/1990 |
| EP | 0505634 | 9/1992 |

(Continued)

OTHER PUBLICATIONS

Siden, Rivka et al., "Epicardial Controlled-Release Verapamil Prevents Ventricular Tahcycardia Episodes Induced by Acute Ischemia in a Canine Model", *J Cardiovascular Pharmacology*, 19, Raven Press Ltd., New York, (1992),798-809.

(Continued)

*Primary Examiner* — Anu Ramana
(74) *Attorney, Agent, or Firm* — Jeffrey R. Ramberg

(57) ABSTRACT

An implantable device for facilitating the healing of voids in bone, cartilage and soft tissue is disclosed. A preferred embodiment includes a cartilage region comprising a polyelectrolytic complex joined with a subchondral bone region. The cartilage region, of this embodiment, enhances the environment for chondrocytes to grow articular cartilage; while the subchondral bone region enhances the environment for cells which migrate into that region's macrostructure and which differentiate into osteoblasts. A hydrophobic barrier exists between the regions, of this embodiment. In one embodiment, the polyelectrolytic complex transforms to hydrogel, following the implant procedure.

14 Claims, No Drawings

Related U.S. Application Data filed on Jul. 19, 2001, now abandoned, which is a continuation-in-part of application No. 09/206,604, filed on Dec. 7, 1998, now Pat. No. 6,264,701, which is a division of application No. 08/242,557, filed on May 13, 1994, now Pat. No. 5,981,825.

(56) References Cited

U.S. PATENT DOCUMENTS

| 2003/0009145 A1 | 1/2003 | Struijker-Boudier et al. |
| 2004/0006146 A1 | 1/2004 | Evans et al. |
| 2005/0261782 A1 | 11/2005 | Hoganson |

FOREIGN PATENT DOCUMENTS

| EP | 0544259 | 6/1993 |
| EP | 0784985 | 7/1997 |
| GB | 2175506 | 12/1986 |
| RU | 2146136 | 3/2000 |
| WO | WO-93/15694 | 8/1993 |
| WO | WO-94/09722 | 5/1994 |
| WO | WO-95/11707 | 5/1995 |
| WO | WO-95/31157 | 11/1995 |

OTHER PUBLICATIONS

Mathew, MD, Joseph P., "A Multicenter Risk Index for Atrial Fibrillation", *JAMA*, 291(14), (Apr. 14, 2005),1720-1729.

Aviles, MD, Ronnier J., et al., "Inflammation as a Risk Factor for Atrial Fibrillation", *Circulation*, 108, (2003),3006-3010.

Yared, MD, Jean-Pierre et al., "Effects of Single Dose, Postinduction Dexamethasone on Recovery After Cardiac Surgery", *Ann Thorac Surg 2000*, 69, (2000),1420-1424.

Halvorsen, MD, Per et al., "The Effect of Dexamethasone on Side Effects After Coronary Revascularization Procedures", *Anesth Analg 2003*, 96, (2003),1578-83.

Grande, et al., "A dual gene therapy approach to osteochondral defect repair using a bilayer implant containing BMP-7 and IGF-1 transduced periosteal cells", *47 Sup. Th Annual Meeting, Orthopaedic Research Society*, Feb. 25-28, 2001, San Francisco, California.

Gao, J et al., "Tissue engineered osteochondral graft using rat marrow-derived mesenchymal stem cells", *47 Sup Th Annual Meeting, Orthopaedic Research Society*, Feb. 25-28, 2001 San Francisco California.

* cited by examiner

DEVICE FOR REGENERATION OF ARTICULAR CARTILAGE AND OTHER TISSUE

CROSS REFERENCE

The present application is a continuation of U.S. patent application Ser. No. 10/830,267, filed Apr. 21, 2004, now U.S. Pat. No. 7,963,997, which is a continuation of U.S. patent application Ser. No. 10/199,961, filed Jul. 19, 2002, now abandoned, which is a continuation-in-part of U.S. patent application Ser. No. 09/909,027, filed Jul. 19, 2001, now abandoned, which is a continuation-in-part of U.S. patent application Ser. No. 09/206,604, filed Dec. 7, 1998, now U.S. Pat. No. 6,264,701, which is in turn a division of U.S. patent application Ser. No. 08/242,557, filed May 13, 1994. now U.S. Pat. No. 5,981,825. The contents of each of the above-noted Patents and applications is hereby fully incorporated herein by reference.

FIELD OF THE INVENTION

The present invention generally relates to the transport and/or culturing of cells, and more specifically to the healing of voids or other defects in bone, cartilage and soft tissue.

BACKGROUND OF THE INVENTION

The medical repair of bones and joints and other tissue in the human body presents significant difficulties, in part due to the materials involved. Each bone has a hard, compact exterior surrounding a spongy, less dense interior. The long bones of the arms and legs, the thigh bone or femur, have an interior containing bone marrow. The material that bones are mainly composed of is calcium, phosphorus, and the connective tissue substance known as collagen.

Bones meet at joints of several different types. Movement of joints is enhanced by the smooth hyaline cartilage that covers the bone ends, by the synovial membrane that covers the hyaline cartilage and by the synovial fluid located between opposing articulating surfaces.

Cartilage damage produced by disease such as arthritis or trauma is a major cause of physical deformity and dehabilitation. In medicine today, the primary therapy for loss of cartilage is replacement with a prosthetic material, such as silicone for cosmetic repairs, or metal alloys for joint realignment. The use of a prosthesis is commonly associated with the significant loss of underlying tissue and bone without recovery of the full function allowed by the original cartilage. The prosthesis is also a foreign body which may become an irritating presence in the tissues. Other long-term problems associated with the permanent foreign body can include infection, erosion and instability.

The lack of a truly compatible, functional prosthesis subjects individuals who have lost noses or ears due to burns or trauma to additional surgery involving carving a piece of cartilage out of a piece of lower rib to approximate the necessary contours and inserting the cartilage piece into a pocket of skin in the area where the nose or ear is missing.

Surgical removal of infected or malignant tissue is disfiguring and can have harmful physiological and psychological effects. Regeneration of soft tissue, or tissue that mimics the natural properties of the removed tissue, can avoid or lessen these untoward consequences. Finally. a device which delivers a therapy could aid the regeneration of tissue, minimize risk of infection, and/or treat any underlying disease or condition.

The foregoing being exemplary, a device according to the teachings of the present invention is expected to add utility in many areas, see Table 1, which is meant to be expansive of the foregoing, and not limiting.

TABLE 1

| Examples of tissues and procedures potentially benefiting from the teachings of the present invention |
|---|
| Bone |
| Bone tissue harvest |
| Spinal arthrodesis |
| Spinal fixation/fusion |
| Osteotomy |
| Bone biopsy |
| Maxillofacial reconstruction |
| Long bone fixation |
| Compression fractures |
| Hip reconstruction/replacement |
| Knee reconstruction/replacement |
| Hand reconstruction |
| Foot reconstruction |
| Ankle reconstruction |
| Wrist reconstruction |
| Elbow reconstruction |
| Shoulder reconstruction |
| Cartilage |
| Mosaicplasty |
| Meniscus |
| Dental |
| Ridge augmentation |
| Third molar extraction |
| Tendon |
| Ligament |
| Skin |
| Topical wound |
| Burn treatment |
| Biopsy |
| Muscle |
| Dura |
| Lung |
| Liver |
| Pancreas |
| Gall bladder |
| Kidney |
| Nerves |
| Artery |
| Bypass Surgery |
| Cardiac catheterization |
| Heart |
| Heart valve replacement |
| Partial organ removal |

In the past, bone has been replaced using actual segments of sterilized bone or bone powder or porous surgical steel seeded with bone cells which were then implanted. In most cases, repair to injuries was made surgically. Patients suffering from degeneration of cartilage had only pain killers and anti-inflammatories for relief.

Until recently, the growth of new cartilage from either transplantation or autologous or allogeneic cartilage has been largely unsuccessful. Consider the example of a lesion extending through the cartilage into the bone within the hip joint. Picture the lesion in the shape of a triangle with its base running parallel to the articular cavity, extending entirely through the hyaline cartilage of the head of the femur, and ending at the apex of the lesion, a full inch (2.54 cm) into the head of the femur bone.

Presently, there is a need to successfully insert an implant device which will assure survival and proper future differentiation of cells after transplantation into the recipient tissue defect. Difficulties have been experienced with engineering the implant environment such that cells may survive, and also with supporting proper cell differentiation.

Presently, for example, cartilage cells, called chondrocytes, when implanted along with bone cells, can degenerate or dedifferentiate into more bone cells. Because hyaline cartilage is an avascular tissue, it must be protected from intimate contact with sources of high oxygen tension such as blood. Bone cells, in contrast, require high oxygen levels and blood. For this reason, the subchondral bone region of the device should be isolated from the cartilage region, at least so far as oxygen and blood are concerned.

Most recently, two different approaches to treating articular lesions have been advanced. One approach such as disclosed in U.S. Pat. No. 5,041,138 is coating bioderesorbable polymer fibers of a structure with chemotactic ground substances. No detached microstructure is used. The other approach such as disclosed in U.S. Pat. No. 5,133,755 uses chemotactic ground substances as a microstructure located in voids of a macrostructure and carried by and separate from the biodegradable polymer forming the macrostructure. Thus, the final spatial relationship of these chemotactic ground substances with respect to the bioresorbable polymeric structure is very different in U.S. Pat. No. 5,041,138 from that taught in U.S. Pat. No. 5,133,755.

The fundamental distinction between these two approaches presents three different design and engineering consequences. First, the relationship of the chemotactic ground substance with the bioresorbable polymeric structure differs between the two approaches. Second, the location of biologic modifiers carried by the device with respect to the device's constituent materials differs. Third, the initial location of the parenchymal cells differs.

Both approaches employ a bioresorbable polymeric structure and use chemotactic ground substances. However, three differences between the two approaches are as follows.

I. Relationship of Chemotactic Ground Substances with the Bioresorbable Polymeric Structure The design and engineering consequence of coating the polymer fibers with a chemotactic ground substance is that both materials become fused together to form a single unit from structural and spatial points of view. The spaces between the fibers of the polymer structure remain devoid of any material until after the cell culture substances are added.

In contrast, the microstructure approach uses chemotactic ground substances and/or other materials, separate and distinct from the macrostructure. The microstructure resides within the void spaces of the macrostructure. Additionally, an embodiment incorporating a microstructure may use materials such as polysaccharides and chemotactic ground substances that are spatially separate from the macrostructure polymer thereby forming an identifiable microstructure, separate and distinct from the macrostructure polymer.

The design and engineering advantage to having a separate and distinct microstructure capable of carrying other biologically active agents can be appreciated in the medical treatment of articular cartilage. RGD attachment moiety of fibronectin is a desirable substance for attaching chondrocytes cells to the lesion. However, RGD attachment moiety of fibronectin is not, by itself, capable of forming a microstructure of velour in the microstructure approach. Instead, RGD may be blended with a microstructure material prior to investment within macrostructure interstices.

II. Location of Biologic Modifiers Carried by a Device with Respect to the Device's Constituent Materials Coating only the polymer structure with chemotactic ground substances necessarily means that the location of the chemotactic ground substance is only found on the macrostructure (e.g., bioresorbable polymer) fibers, thereby affording a two dimensional presentation. The microstructure approach uses the microstructure to carry biologic modifiers (e.g., growth factors, morphogens, drugs, etc.), however the presentation is analogous to a three dimensional presentation. Therefore, the coating approach has a limited capacity to carry biologic modifiers with the biodegradable polymeric structure.

III. Initial Location of the Parenchymat Cell

Because the coating approach attaches the chemotactic ground substances to the surfaces of the structure and has no microstructure resident in the void volume of the device, the coating approach precludes the possibility of establishing a network of extracellular matrix material, specifically a microstructure, within the spaces between the fibers of the polymer structure once the device is fully saturated with cell culture medium. The coating approach predetermines that any cells introduced via culture medium will be immediately attracted to the surface of the structure polymer and attach thereto by virtue of the chemotactic ground substances on the polymer's surfaces.

The consequence of confining chemotactic ground substances to only the surfaces of the polymeric structure places severe restrictions on the number of cells that can be accommodated by the coated device.

In contrast with the coating approach, the microstructure approach, by locating chemotactic ground substances in the void spaces of the device, makes available the entire void volume of the device to accommodate the attracted cells which then lay down their own extracellular matrix resulting in a more rapid and complete tissue regrowth or ingrowth.

One of the many objects of this invention, as will be discussed, is to protect and aid cellular ingrowth or regeneration of various types of new tissue, as well as providing methods of concurrent delivery of therapies and other treatments.

SUMMARY OF THE INVENTION

A device of the present invention is a prosthesis or implant for in vivo culturing of tissue cells in a diverse tissue or homogeneous lesion. The entire macrostructure, or a major portion, of this device may be composed of a bioresorbable polymer. Alternatively, the microstructure may be the only portion of the device which is resorbable, if a microstructure was employed at all. Alternatively, it is also conceived that the device could be used to culture cells via in vitro techniques known in the art for later in vivo transplantation.

A device of the present invention may include a macrostructure, microstructure, free precursor cells cultured in vitro or from tissue, or biologically active agents. "Biologically active agents" as used in this disclosure meaning, but not limited to, growth factors, morphogens, drugs, proteins, cells, cellular components. signaling proteins, signal transduction factors, and other therapeutic agents.

An anatomically specific device of the present invention could be designed primarily for treating cartilage and bone lesions and, when used for that purpose, preferentially has two main regions: a cartilage region and a subchondral bone region. Alternatively, it is envisioned that a singular region may be employed to repair defects in other areas and types of host tissue. Likewise, additional regions may be used to "bridge" tissue of distinct histological variation, as well as other variations.

A first embodiment of the present invention comprises a cartilage region which has a macrostructure and a microstructure. The selective concentration gradient of material in the microstructure may be selectively varied within certain regions of the macrostructure voids to affect different biologic characteristics and tissue requirements.

The microstructure of a single device of the present invention may be composed of multiple different materials, some without chemotactic properties, in different regions of macrostructure void space depending upon varying tissue and biologic characteristics and requirements.

The subchondral bone region of this embodiment includes a macrostructure composed of a biologically acceptable, polymer (preferably bioresorbable) arranged as a one piece porous body with "enclosed randomly sized, randomly positioned and randomly shaped interconnecting voids, each void communicating with all the others, and communicating with substantially the entire exterior of the body" (quoted portion from U.S. Pat. No. 4,186,448). In the preferred embodiment as described here, the internal three dimensional architecture of the macrostructure resembles that of cancellous bone. In other embodiments, the internal 3-D architecture of the macrostructure may be highly ordered, as described in U.S. Pat. No. 5,981,825, to replicate the spatial patterns of other tissues or to create a tissue pattern required for performance of specific anatomic and/or physiologic functions. In one preferred embodiment, polylactic acid (PLA), fabricated in the 3-D architecture of intercommunicating voids described above forms the macrostructure. Other members of the hydroxy acid group of compounds can also be used as can any bioresorbable polymer, natural or synthetic, if fabricated into a similar architecture. Alternatively, the macrostructure could be fabricated from natural materials (e.g., bone, coral, or collagen), ceramic materials (whether natural or synthesized, e.g., hydroxyapatite or tricalcium phosphate), or other materials, such as those shown in Tables 2 and 3.

The gross, or macro, structure of this embodiment attempts to address three major functions for chondrogenesis and osteogenesis: 1) restores mechanical architectural and structural competence; 2) provides biologically acceptable and mechanically stable surface structure suitable for genesis, growth and development of new non-calcified and calcified tissue; and 3) functions as a carrier for other constituents of the present invention which do not have mechanical and structural competence.

The microstructure of this embodiment may be composed of various polysaccharides which, in a preferred form, is alginate but can also be hyaluronic acid (abbreviated by HY). Interstices of the polylactic acid macrostructure of the body member are invested with the microstructure substance which may be in the form of a velour having the same architecture of interconnecting voids as described for the macrostructure, but on a microscopic scale. Functions of the microstructure (e.g., HY) may include: 1) attraction of fluid blood throughout the device; 2) chemotaxis for mesenchymal cell migration and aggregation; 3) carrier for osteoinductive and chondro-inductive agent(s); 4) generation and maintenance of an electronegative wound environment; 5) agglutination of other connective tissue substances with each other and with itself, and 6) coating of the edges of the macrostructure to minimize or prevent foreign body giant cell responses, as well as other adverse responses to the implant. Other examples of suitable microstructures are fibronectin and, especially for the reconstruction of articular cartilage, an RGD attachment moiety of fibronectin.

The osteoinductive agent, bone morphogenetic protein, has the capacity to induce primitive mesenchymal cells to differentiate into bone forming cells. Another osteogenic agent, bone derived growth factor, stimulates activity of more mature mesenchymal cells to form new bone tissue. Other biologically active agents which can be utilized, especially for the reconstruction of articular cartilage, include but are not limited to transforming growth factor beta (TGF beta) and basic fibroblast growth factor (bFGF).

In this first embodiment, as well as the balance of the specification and claims, the term "bioabsorbable" is frequently used. There exists some discussion among those skilled in the art, as to the precise meaning and function of bioabsorbable material (e.g., polymers), and how they differ from resorbable, absorbable, bioresorbable, biodegradable, and bioerodable materials. The current disclosure contemplates all of these materials, and combines them all as bioresorbable. Any use of an alternate disclosed in this paragraph is also meant to describe and include all of the others.

In a second embodiment of the present invention, the device acts as a transport device for precursor cells harvested for the production of connective tissue. The device can be press fit into the site of lesion repair, and subsequently charged with a solution of cells, growth factors, etc., as will be described later. Another aspect of this embodiment is that the microstructure velour can be treated with an RGD attachment moiety of fibronectin that facilitates the attachment of free precursor cells to be carried to the lesion repair site.

Additional embodiments of the present invention allow for the tailoring of mechanical and physical properties through the use of additions of other polymers, ceramics, microstructures and processes (e.g., void tailoring, cross-linking, and pre-stressing). Additionally, the delivery of therapies aids regeneration of tissue, minimizes procedural discomfort to the patient, and treats underlying disease.

DESCRIPTION OF THE PREFERRED EMBODIMENTS

A device and methods according to the preferred teachings of the present invention are disclosed for treating mammalian bone and cartilage and soft tissue deficiencies, defects, voids and conformational discontinuities produced by congenital deformities, osseous and/or soft tissue pathology, traumatic injuries, and accidental, surgical, or functional atrophy. The primary purpose of this implant device is to provide the means by which chondrocytes, or other cells, and their attendant synthesis, cultured in vitro, can be transported into a defect and be safely established therein. Thus, the most preferred embodiments of the present invention provides means to regenerate a specific form of tissue.

A first embodiment of the present invention consists of two main parts, the cartilage region and the subchondral bone region joined at an interface surface. Each of the cartilage and the subchondral bone regions of the device includes a macrostructure composed of a bioresorbable polymer either as homogeneous polymers or combinations of two or more co-polymers from groups of, for example, poly (alpha-hydroxy acids), such as polylactic acid or polyglycolic acid or their co-polymers, polyanhydrides, polydepsipeptides, or polyorthoester. Devices fabricated for prototypes of animal studies to-date have been fabricated from the homopolymer D, D-L, L-polylactic acid, and polyelectrolytic complexes.

The bioresorbable polymer in the subchondral bone region in this form is in the architecture of cancellous bone such as of the type described in U.S. Pat. Nos. 4,186,448 and 5,133,755, which are hereby incorporated herein by reference.

The architecture of the cartilage region may be formed utilizing established techniques widely practiced by those skilled in the art of bioresorbable polymers. These methods include injection molding, vacuum foaming, spinning hollow filaments, solvent evaporation, soluble particulate leaching or combinations thereof. For some methods, plasticizers may be required to reduce the glass transition temperature to low enough levels so that polymer flow will occur without decomposition.

The macrostructure polymer of the cartilage region is joined or bound to the macrostructure polymer of the subchondral bone region by a process such as heat fusion which does not involve the use of solvents or chemical reactions between the two polymer segments. The resulting union between the two architectural regions is very strong and can withstand any handling required to package the device as well as any forces delivered to it as a result of the implantation technique without distorting the device's internal architecture of void spaces.

In former constructs such as U.S. Pat. No. 5,133,755, the preferred microstructure was hyaluronan which is synonymous with hyaluronic acid, hyaluronate, HA and HY. The hyaluronan was distributed uniformly throughout the internal void volume of the device. According to the teachings of the present invention, an option is provided of selecting whether or not the microstructure, if any, should be dispersed throughout all the void spaces depending on whether the arrangement is beneficial to the tissues being treated. A device of the present invention permits incomplete dispersal as desired or complete dispersal throughout the entire void volume of the device but expressing concentration gradients of microstructure material as a means of controlling transplanted cell population numbers within the device's internal domains.

A dry filamentous velour of chemotactic ground substance, for example RGD attachment moiety of fibronectin carried by hyaluronic acid or alginic acid velour, may be established within the void spaces of the device. Upon saturation with water, water-based cell culture media or fluid blood, the dry velour of chemotactic ground substance is dissolved into a highly viscous gel which maintains the chemotactic ground substance as a network of dissolved polysaccharide strands, still suspended within the void volume of the polymeric macrostructure. It is envisioned that other therapies may also be carried by this gel, as will be discussed later.

If the cell culture media is a fluid which saturates the device and creates the gel, then those cells suspended in the culture medium will be temporarily trapped within the gel due to the gel viscosity. The degree of gel viscosity and the length of time the gel maintains significantly high viscosities will aid in cellular propagation, i.e., restraining the transported cells by means of microstructure gel gives the cells additional time to execute biological processes. Additionally, this restraint can be used to modulate the delivery rate of the therapy.

The volume of space once occupied by the microstructure gel can then be occupied by the interstitial fluid and increased numbers of cells. In the articular cartilage regeneration of the preferred form, it is desired to protect the transplanted cells from access to fluid blood and collateral circulation. In other tissue regeneration situations, however, it may be desirable or beneficial to attract fluid blood into the device's interstices as quickly as possible. In these situations, therefore, fibrin (i.e. blood clot), endothelial cells, or other materials or therapies may be loaded into the device, or gained from sources of viable collateral circulation.

Certain embodiments of the present invention depart from prior practice by strategically positioning the microstructure material in that specific portion of the device which performs particular functions unique to the mature anatomy being regenerated in that vicinity. Such segregation of microstructure material within the device is based on the need to endow one portion of the device with special biologic functions that must be isolated from the remainder of the implanted device.

In yet another embodiment of the present invention, the microstructure has a secondary purpose to present enough chondrocytes to the subchondral bone region immediately adjacent to the cartilage region to insure that a competent osteo-chondral bond is established between the newly developed cartilage and the newly developed bone.

Within the inventive concept of several embodiments of the present invention is the establishment of variations in the concentration of microstructure within the void space network of the macrostructure in order to assure that the therapeutic elements and biologically active agents brought from in vitro culture, or loaded as will be described later, are present within the final device in greatest quantity where they are most needed. Such variations in concentration can be accomplished by varying concentrations of microstructure solutions prior to investment into macrostructure voids of the device or regions thereof before joining, as well as other methods known in the art.

In yet another embodiment of the current invention, the cartilage region of the construct comprises a polyelectrolytic complex (PEC). This complex preferably comprises polyanions and polycations. Since certain of these complexes in their dry states may not have sufficient strength to allow handling, processing may be required to increase their structural integrity. This processing can follow the methods previously disclosed, as well as various other generic techniques known to those skilled in the art. Because of the unique bonding structures contained in PEC's, some researchers have referred to them as poly-ionic complexes (PIC's). For this reason, the current disclosure recognizes no difference between the PEC and the PIC.

The PEC may be formed from glycosaminoglycans (GAG's) and polycations as well as other similarly structured compounds. While having the requisite electron affinity noted above for bonding, some of the sulfonated GAG's may not be effective in attracting the appropriate cell-types. In a preferred embodiment, the PEC is made from hyaluronic acid (HY), a non-sulfonated GAG, and chitosan. The PEC may be fabricated by various methods known to those skilled in the art, one such method follows.

The strong negative charge associated with HY is provided by the carboxylic acid group (—COOH) of its glucuronic acid moiety. When exposed to pH levels below about 6.5, the amine groups of chitosan molecules become protonated, thus rendering the molecules soluble in water and providing them with a strong positive charge that attracts negatively-charged molecules (e.g., HY, etc.) and thus forming electrostatic interactions. When a solution of protonated chitosan is exposed to a solution of HY, an insoluble precipitate (the PEC) is formed.

In yet another PEC embodiment, the PEC is made from hyaluronic acid and collagen (i.e., collagen type I or type II or type III, etc.), where collagen acts as a polycation. Collagen, an amphoteric species, functions as a cation when treated similarly to chitosan, as described above, or by other methods known to those skilled in the art.

The collagen may be supplied to the PEC in the form of demineralized bone matrix (DBM) material. It is realized that DBM also comprises, in addition to collagen, morphogens and growth factors, as secondary constituents. It is also recognized that these secondary constituents may add to the overall tissue regenerative capacity of the implant.

Other glycosaminoglycans such as, but not limited to, heparin, chondroitin-4-$SO_4$, chondroitin-6-$SO_4$, dermatan-$SO_4$, and keratin sulfate may also be used as a complement to or in place of hyaluronic acid, in these various embodiments.

In a similar embodiment, the macrostructure or microstructure, if any, of any region(s) may comprise chitosan, not bound in the aforementioned PEC. This embodiment, herein referred to as a "regeneration complex" may be formed by the techniques discussed herein, as well as those others known in the art. Alternatively, this regeneration complex may comprise a protein (e.g., type I collagen, type II collagen, type III collagen, carrageenan, fibrin, elastin, resilin, abductin, demineralized bone, or agarose), polysaccharide (e.g., cellulose, starches, chitosan, alginate, sulfated glycosaminoglycans, or non-sulfated glycosaminoglycans), a lipid (e.g., phospholipid, triglyceride, waxes, steroids, prostaglandins, or terpenes), a synthetic polymer (e.g., polylactide, polyglycolide, polyurethane, polyethylene, poly-e-caprolactone, polyvinyl alcohol, polycarbonate, or PTFE), ceramic (e.g., bioglass or calcium phosphate), singularly or as a mixture thereof. These alternatives may be formed by methods similar to those used for monolithic chitosan, as well as those previously disclosed.

By way of example, one embodiment utilizes a resorbable polymer macrostructure and hyaluronic acid microstructure in one region that is adjacent to a collagen regeneration complex. The collagen can be of several varieties as well as composites of thereof. Kensey Nash Corporation (Exton, Pa.) manufactures soluble collagen known as Semed S, fibrous collagen known as Semed F, and a composite collagen known as P1076. Each of these materials would be suitable for this embodiment. This embodiment may also include additives (e.g., sodium hyaluronate) blended or composited with the collagen slurry and co-lyophilized to create a material with desirable mechanical and chemical properties. The regeneration complex may undergo chemical, thermal, or radiation treatments in order to cross-link the material to provide desired strength and/or degradation qualities. Additionally, a calcium mineral such as hydroxyapatite or a growth factor, such as TGF-beta, may be added to the regeneration complex or to the neighboring region(s) in order to customize the implant for use in a bone or cartilage regeneration device. All of the foregoing alterations of the device's mechanical, chemical, or biological properties and responses are referred to as "matrix matching."

Matrix matching may also be achieved by processes other than cross-linking. For example, pore size, shape, and population may be engineered, by degree and rate of lyophilization, the polymer structure may be plastically strained or directionally treated to impart anisotropy or the like. As has been described, macrostructure and microstructural additions can greatly affect the degree of matrix matching; not only by the properties of addition (i.e., relative to the properties of the host matrix), but also by the relative amount placed therein (i.e., relative to total amount of macrostructure, or total amount of void space available to be filled by the microstructure).

Such matrix matching may be employed to approximate or nearly approximate the property of the host or other desired tissue to be regenerated. Alternatively, where the aforementioned result is not feasible, desirable (e.g., due to patient discomfort, allowances for inflammation of existing tissue, or sacrificing some strength for added toughness), or practical, the degree of matrix matching may be intentionally limited. While several exemplary embodiments have been given, additional composite elements and additives are contemplated (e.g., including PEC complexes and regeneration complexes, and combinations thereof), many of which are listed in Tables 2 and 3. Various other processes are also known in the art, which may be used alone, or in combination with any of the foregoing, in order to accomplish this same effect and result.

The tissue resulting after ingrowth or regeneration may also be matrix matched, that is, the tissue strength, density, and pliability may be altered by the matrix used. Ideally, the device would be matrix matched, and so would the regenerated tissue, although matrix matching refers to either, as is discussed in more detail later.

Another similar embodiment utilizes a demineralized bone matrix macrostructure and hyaluronic acid microstructure in one region that is adjacent to a chitosan PEC, as is described above, on a first side and a chitosan PEC on a second diametrically opposed side. This multi-layered implant would have the ability to regenerate cancellous bone through its middle region while regenerating cortical bone or cartilage on the end regions. Bone or cartilage are used in this example, but various other tissues are contemplated, and the regions may be arranged other than uniaxially. Additionally, an embodiment is contemplated wherein the demineralized bone may be replaced with porous hydroxyapatite if a stronger implant or longer-lasting type implant is desired.

In yet another embodiment, collagen may be used, for example, in the form of a porous fabric, to define a macrostructure. The porous fabric can be created to allow for specific pore size and separation. The fabric maintains an architecture that is suitable and similar to the atmosphere that chondrocytes are exposed to in host tissue. This macrostructure presents the structural integrity necessary to supply a homeostatic atmosphere for chondrocyte viability. This allows regenerative cascades to occur and allows for replication of damaged tissue. In addition, elements may be added to the macrostructure to create one microstructure. An example of this can be hyaluronic acid, demineralized bone matrix DBM, etc. Regardless of whether or not a microstructure is used, the macrostructure region may be attached to a second region via a porous polymeric film.

This film may be interposed between the first (e.g., collagen) and second regions at their interface, thereby increasing the strength of the bond. This interposition may be formed in a manner similar to the following example; a porous or non-porous film may be created of the desired polymer to create the needed bond. The thin film may be placed between the two regions to allow fixation in such manner where heat, UV, etc. may be used to combine the two materials.

Additionally, the polymer film may be constructed with the use of a solvent to create the film. This solution/slurry/suspension/gel emulsion can be applied to both or either material, with varying concentrations to bind the two materials. An example of one such procedure would be to apply the solution in such a fashion where a brush would be used for application. By way of example and not limitation, other manners may be employed, including spraying, dipping, etc. Therefore, these embodiments describe the application of the film in the liquid and/or solid states, and this disclosure contemplates other methods of polymer deposition known to those skilled in the art (e.g., spraying, dipping, heat application, UV, etc.)

In the foregoing PEC and regeneration complex embodiments, it is also contemplated that these devices will be implanted into a tissue requiring regeneration of one or multiple tissues. The devices of this disclosure may be implanted in a variety of ways. In one embodiment, the implant will be pressed into a defect site and, as will be discussed later in greater detail, will expand in apparent volume thus maintaining positive contact with host tissue. Other methods of implantation include suturing the implant into place, suturing a flap over the implant (such as a periosteal flap), using a glue or sealant (such as a fibrin glue), screws and fixturing, containing the implant within a separate device which is screwed, glued (e.g. thrombin, cyanoacrylate, etc.), press-fitting in place (such as an interbody fusion cage), or by other methods known to those skilled in the art.

Additionally, the shape or contouring of the implant can be used to hold the implant in place. In one embodiment, the implant may be created in the shape of a screw or a barb by using a mold, by cutting away the material, or by other methods known to those skilled in the art. In another embodiment, the contouring is created only in a region of the implant where tissue will regenerate the fastest. The contouring is purposely designed to provide resistance to shear, tensile, compressive, torque, and other forces acting to dislodge the implant. While some applications require contouring in only one region, other applications will require multiple regions of contouring.

The foregoing PEC and regeneration complex embodiments will have certain beneficial reactions following implant. That is, among other things, particular of these formations will imbibe water-based fluids in the implant vicinity. This fluid infusion will cause one or more regions of the implant to swell. Swelling may be important for securement reasons, as previously discussed, or for its affect on biological activity.

The swelling of these particular implant compositions is nearly equiaxial, that is, proportional in all directions to dimensions of the original, dry construct. Upon prolonged hydration, void spaces of the dry construct become occluded by the gel generated when water becomes bound to fibers of the PEC and additional water becomes entrapped between hydrated PEC filaments. Thus, those skilled in the art refer to this resulting structure as a hydrogel. The hydrogel medium endows its region of the device with several benefits that include, but are not limited to: (i) restricting trans-implant communication of biologically active agents; (ii) allowing its cargo of biologically active agents unrestricted access to host tissues immediately after implantation while progressively restricting this access over time; (iii) providing a depot of biologically active agent for access by cells entering the hydrogel region; and (iv) establishing the early microenvironment for cell migration into the defect (e.g., chemotaxis). The minimization of the access to these agents, however, is not detrimental to the function of the implant, since mass transfer (i.e., transfer of gases, nutrients, and cell waste products) occurs through hydrogels, and the cellular functions of respiration and metabolism continue.

In the foregoing PEC and regeneration complex embodiments, it is contemplated that the subehondral bone region comprises a resorbable polymer (polymer being synthetic or organic/natural, e.g., see Table 2) as well as other non-resorbable or non-polymeric materials (e.g., see Table 3); additionally, these materials may be used for a PEC region macrostructure, if one is employed. The macrostructure being a structure comprising voids, in which the PEC could be invested, along with other materials and therapies. In this type of embodiment, the materials and therapies are referred to collectively as the microstructure. The macrostructure and microstructure are also tailorable by other additions (e.g., see those materials and compounds listed in Tables 2 and 3).

In another embodiment, the void spaces within the macrostructure or microstructure, of any region, cause cellular regeneration effects by the size and/or shape thereof. That is, the relative size of the void space can affect the resulting cellular structure that is generated, or likewise the shape of the void space can affect cellular structure. Thus, engineering the size or shape of void spaces to stress or constrict cellular function can influence forms of regenerated tissue.

Similarly, the mechanical properties (e.g., density, hardness, modulus of elasticity, or compressive stiffness) or physical properties (e.g., macrostructure void, microstructure or a void therein, or cell attachment aiding material which is in the microstructure) of the host structure can alter the cellular reproduction type or phenotype. This is expected to be caused by the interaction between the host material and the endocellular fibrils, but other actions and reactions are anticipated to contribute to this effect. This interaction may be utilized to tailor the resulting cell type, by tailoring the host material's mechanical or physical properties.

TABLE 2

Examples and Sub-types of Bioresorbable Polymers for Construction of the Device Macrostructure and/or Microstructure of the Current Invention Aliphatic polyesters
Bioglass
Cellulose
Chitin
Collagen
    Types 1 to 20
    Native fibrous
    Soluble
    Reconstituted fibrous
    Recombinant derived
Copolymers of glycolide
Copolymers of lactide
Elastin
Fibrin
Glycolide/l-lactide copolymers (PGA/PLLA)
Glycolide/trimethylene carbonate copolymers (PGA/TMC)
Hydrogel
Lactide/tetramethylglycolide copolymers
Lactide/trimethylene carbonate copolymers
Lactide/.epsilon.-caprolactone copolymers
Lactide/.sigma.-valerolactone copolymers
L-lactide/dl-lactide copolymers
Methyl methacrylate-N-vinyl pyrrolidone copolymers
Modified proteins
Nylon-2
PHBA/.gamma.-hydroxyvalerate copolymers (PHBA/HVA)
PLA/polyethylene oxide copolymers
PLA-polyethylene oxide (PELA)
Poly (amino acids)
Poly (trimethylene carbonates)
Poly hydroxyalkanoate polymers (PHA)
Poly(alklyene oxalates)
Poly(butylene diglycolate)
Poly(hydroxy butyrate) (PHB)
Poly(n-vinyl pyrrolidone)
Poly(ortho esters)
Polyalkyl-2-cyanoacrylates
Polyanhydrides
Polycyanoacrylates
Polydepsipeptides
Polydihydropyrans
Poly-dl-lactide (PDLLA)
Polyesteramides
Polyesters of oxalic acid
Polyglycolide (PGA)
Polyiminocarbonates
Polylactides (PLA)
Poly-l-lactide (PLLA)
Polyorthoesters
Poly-p-dioxanone (PDO)
Polypeptides
Polyphosphazenes
Polysaccharides
Polyurethanes (PU)
Polyvinyl alcohol (PVA)
Poly-.beta.-hydroxypropionate (PHPA)
Poly-.beta.-hydroxybutyrate (PBA)
Poly-.sigma.-valerolact-one
Poly-.beta.-alkanoic acids
Poly-.beta.-malic acid (PMLA)
Poly-.epsilon.-caprolactone (PCL)
Pseudo-Poly(Amino Acids)
Starch Trimethylene carbonate (TMC)
Tyrosine based polymers

TABLE 3

Examples of alternative materials that may be used for the macrostructure and/or microstructure of the current invention Alginate
Bone allograft or autograft
Bone Chips
Calcium
Calcium Phosphate
Calcium Sulfate
Ceramics
Chitosan
Cyanoacrylate
Collagen
Dacron
Demineralized bone
Elastin
Fibrin
Gelatin
Glass
Gold
Glycosaminoglycans
Hydrogels
Hydroxy apatite
Hydroxyethyl methacrylate
Hyaluronic Acid
Liposomes
Mesenchymal cells
Nitinol
Osteoblasts
Oxidized regenerated cellulose
Phosphate glasses
Polyethylene glycol
Polyester
Polysaccharides
Polyvinyl alcohol
Platelets, blood cells
Radiopacifiers
Salts
Silicone
Silk
Steel (e.g. Stainless Steel)
Synthetic polymers
Thrombin
Titanium
Tricalcium phosphate It is also contemplated that the PEC region, or the regeneration complex region, may be used alone (i.e., without a subchondral bone, or other region) or with a microstructure contained therein. Furthermore, it is recognized that when two or more regions are joined, as discussed in the various embodiments herein, there may exist a zone that is chemically or structurally distinct from either of, or one of, the regions. This may be incidental to the processing methods employed, or the natural reaction of the body's incorporation of the implant. That is, the zone may be intentional or a planned or unplanned result. For example, zones incorporating barriers and other active agents are within the scope of the invention. Furthermore, a zone incorporating a hydrophobic barrier wherein the surface properties of the macrostructure are altered (e.g., rendered hydrophobic) without altering the geometry or mechanical characteristics of the macrostructure is envisioned.

It is further contemplated that gene therapy may be used with PEC constructs, or similar devices for the regeneration of bone and soft tissue. Gene therapies are currently of two primary types, and are both together hereinafter referred to as "gene therapy" or "engineered cells". However, others are anticipated. The primary methodologies and basic understandings are described herein (see also Table 4).

First, nucleic acids may be used to alter the metabolic functioning of cells, without altering the cell's genome. This technique does not alter the genomic expressions, but rather the cellular metabolic function or rate of expression (e.g., protein synthesis).

Second, gene expression within the host cell may be altered by the delivery of signal transduction pathway molecules.

In a preferred embodiment, mesenchymal stem cells are harvested from the patient, and infected with vectors. Currently, preferred vectors include phages or viri (e.g., retrovirus or adenovirus). This preferred infection will result in a genetically engineered cell, which may be engineered to produce a growth factor (e.g., insulin like growth factor (IGF-1)) or a morphogen (e.g., bone morphogenic protein (BMP-7)), etc. (see also those listed in Table 4). Methods of infection as well as specific vectors are well known to those skilled in the art, and additional ones are anticipated. Following this procedure, the genetically engineered cells are loaded into the implant. Cytokines as described and used herein are considered to include growth factors.

Loading of the cells in this embodiment may be achieved prior to, during, or immediately following the implantation procedure. Loading may be achieved by various methods including, but not limited to, by injecting a solution containing the engineered cells into the implant, by combining the cells with the macrostructure, or by any void filling component, or by themselves, in the void spaces of any of the regions. Prior to the loading of fluid, whether by manual injection or by infiltration from the implant site, the PEC is referred to as being in a "dry state."

Other therapies, including but not limited to drugs, biologically active agents, and other agents, may also be utilized in or with the PEC, or any other associated or adjoined region (e.g., macrostructure or microstructure); either to aid the function of the PEC and/or any other associated or adjoined region or to cause other stimuli. The drugs, biologics, or other agents may be naturally derived or otherwise created (e.g. synthesized). For example, growth factors can be derived from a living being (e.g. autologous, bovine derived, etc.), produced synthetically, or made using recombinant techniques (e.g. rhBMP-2). Regardless of the time of investment or incorporation of these materials, they may be in solid particulate, solution gel or other deliverable form. Utilizing gel carriers may allow for the materials to be contained after wetting, for some tailorable length of time. Furthermore, additions may be incorporated into the macrostructure during manufacture or later. The incorporations may be made by blending or mixing the additive into the macrostructure or microstructure material, by injection into the gel or solid material, or by other methods known to those skilled in the art. Another method of incorporating additives, biologics and other therapies, into the macrostructure or microstructure of one or more regions of the device is through the use of micro spheres.

The term "microsphere" is used herein to indicate a small additive that is about an order of magnitude smaller (as an approximate maximum relative size) than the implant. The term does not denote any particular shape. It is recognized that perfect spheres are not easily produced. The present invention contemplates elongated spheres and irregularly shaped bodies.

Microspheres can be made of a variety of materials such as polymers, silicone and metals. Biodegradable polymers are ideal for use in creating microspheres (e.g., see those listed in Tables 2 and 3). The release of agents from bioresorbable microparticles is dependent upon diffusion through the microsphere polymer, polymer degradation and the microsphere structure. Although most any biocompatible polymer could be adapted for this invention, the preferred material would exhibit in vivo degradation. It is well known that there can be different mechanisms involved in implant degradation like hydrolysis, enzyme mediated degradation, and bulk or surface erosion. These mechanisms can alone or combined influence the host response by determining the amount and character of the degradation product that is released from the implant. The most predominant mechanism of in vivo degradation of synthetic biomedical polymers like polyesters, polyamides and polyurethanes, is generally considered to be hydrolysis, resulting in ester bond scission and chain disruption. In the extracellular fluids of the living tissue, the accessibility of water to the hydrolysable chemical bonds makes hydrophilic polymers (i.e. polymers that take up significant amounts of water) susceptible to hydrolytic cleavage or bulk erosion. Several variables can influence the mechanism and kinetics of polymer degradation, including but not limited to material properties like crystallinity, molecular weight, additives, polymer surface morphology, and environmental conditions. As such, to the extent that each of these characteristics can be adjusted or modified, the performance of this invention can be altered.

In a homogeneous embodiment (i.e., monolithic or composite of uniform heterogeneity) of a therapy delivering implant material, the device provides continuous release of the therapy over all or some of the degradation period of the device. In an embodiment incorporating microspheres, the therapy is released at a preferential rate independent of the rate of degradation of the matrix resorption or degradation. In certain applications, it may also be necessary to provide a burst release or a delayed release of the active agent. The device may also be designed to deliver more than one agent at differing intervals and dosages. This time-staged delivery also allows for a dwell of non-delivery (i.e., a portion not containing any therapy), thereby allowing alternating delivery of non-compatible therapies. Delivery rates may be affected by the amount of therapeutic material, relative to the amount of resorbing structure, or the rate of the resorption of the structure.

Time-staged delivery may be accomplished via microspheres, in a number of different ways. The concentration of therapeutic agent may vary radially, that is, there may be areas with less agent, or there may be areas with no agent. Additionally, the agent could be varied radially, such that one therapy is delivered prior to a second therapy allowing the delivery of noncompatible agents, with the same type of sphere, during the same implant procedure. The spheres could also vary in composition. That is, some portion of the sphere population could contain one agent, while the balance may contain one or more alternate agents. These differing spheres may have different delivery rates. Finally, as in the preceding example, there could be different delivery rates, but the agent could be the same, thereby allowing a burst dose followed by a slower maintained dose.

In a time-phased delivery embodiment, the implant may be constructed to effect a tailored delivery of active ingredients. Both the presence of the implant and the delivery of the select agents are designed to lead to improvements in patients with tissue defects, as a result of delivering in no certain order: (1) a substratum onto which cells can proliferate, (2) a drug or biologically active agent which can act as a signaling molecule which can activate a proliferating or differentiating pathway, (3) a drug or biologically active agent which may act as a depot for nutrients for proliferating and growing cells, and (4) a drug or biologically active agent which will prevent an adverse tissue response to the implant, or provide a therapy which reduces infection and/or treats an underlying disease or condition.

In yet another embodiment, a matrix matched device is designed to mimic the properties of the host tissue and/or shape of any removed tissue, immediately upon implant or shortly after absorbing bodily fluids into the device's void network, or microstructure (if one is employed). The changing properties of certain polymers, following absorption or adsorption, of fluids is well known in the art. The device will afford a more natural feeling (than traditional implants), and minimize the feeling of a foreign body to the patient. As the device resorbs, it will foster the ingrowth or regeneration of tissue with properties matching or nearly approximating the host tissue, such that after a certain period of time (e.g., about two months to two years), the site of the procedure may have the pre-procedure look and feel restored. This embodiment may be especially beneficial for patients who have organs, tumors, or other tissue masses removed, and affords all of the therapeutic modes of the previous embodiments.

The device may matrix match the resulting tissue by preferentially altering the resulting scar tissue that is developed. Normal scar tissue occurs as fibrous bundles, with properties varying widely from the normal host tissue, and the structure of the implant device in this embodiment will tailor the growth of the scar tissue such that its properties will approach that of the native tissue. The structure of the implant is used to train the tissue, such that scar tissue forms in a non-bundled form (e.g., fibrous strands, more linear arrays, or smaller or thinner bundles), and the structure has enough integrity to support the growing tissue such that it does not contract non-uniformly, thereby avoiding or minimizing the disfiguring characteristics caused by shrinking of the tissues during final stages of growth and/or bundling. Additionally, this physical or geometric modeling of tissue may be aided by the delivery of a targeted therapy.

In the foregoing embodiments, it is envisioned that therapy delivery may be by way of incorporation of the therapy into the device matrix, macrostructure, microstructure, or microspheres (regardless of where located), and regardless of whether the therapy was delivered uniformly, time-staged, or as a burst dose. These methods of therapy delivery are localized in nature, as opposed to systemic approaches, that are necessarily delivered via the blood-stream. These systemic approaches concomitantly deliver therapies to various tissue and organs for which they were not intended. Localized delivery may allow higher doses, at the target site, than are tolerable to the body as delivered systemically. Chemotherapeutic treatment for certain cancers as well as other diseases may particularly be amenable to this type of therapy delivery, although various other procedures, not limited to those in Table 1, may benefit. Secondary therapies, or therapies delivered simultaneously with primary therapies, may be beneficial to reduce or eliminate side-effects of the primary therapy.

It is envisioned that time-staged delivery, whether achieved by a preferred placement of therapy within the macrostructure, microstructure, or microsphere, would allow staging of treatment, one of which stages may actually be detrimental to cell growth and proliferation, prior to the delivery of therapies that aid in tissue ingrowth or regeneration. Furthermore, tissue ingrowth and regeneration may have stages, such as, the initial nurturing therapy followed by rapid growth and proliferation aids.

As an example, Cisplatin and Paclitaxel are commonly used together in chemotherapeutic applications. These embodiments could deliver Paclitaxel at high dose rates initially, followed by lower dose rates of Cisplatin, which would occur over longer periods of time. It is also envisioned by this invention that the first therapy may be housed in a microstructural element (e.g., Paclitaxel) while the second therapy (e.g., Cisplatin) is housed in the matrix macrostructure. The slower resorbing macrostructure would supply the localized dose of the second therapy over the entire time during which any of the macrostructure remained.

In yet another embodiment, time-staged delivery or secondary therapy delivery may allow the function of tissue (e.g., organ such as the liver, etc.) to be replaced or supported, prior to, or concurrent with, regrowth or regeneration of diseased or removed tissue, or cellular transplant, which may be accomplished by the foregoing embodiments. This support may allow the tissue to slowly regain organic function, or reassume total function, whereas the otherwise diminished capacity may lead to total organ failure. Additionally, this support function therapy may be utilized to counteract a side effect of the primary therapy. As a non-limiting example, it may be used to support liver function during chemotherapy. The aforementioned localized delivery, together with secondary support, may allow the use of drugs not otherwise tolerated, or current drugs in greater dosages.

This type of cellular transplant embodiment may incorporate cells in any of the various regions, as disclosed in the other embodiments, or other sites within the implant (e.g., macrostructure, microstructure, void space, or microsphere). Additionally, therapies may be located in any of these regions.

TABLE 4

Examples with Some Sub-types of Biological, Pharmaceutical, and other Therapies Deliverable via the Device in Accordance with the Present Invention Adenovirus with or without genetic material
Angiogenic agents
Angiotensin Converting Enzyme Inhibitors (ACE inhibitors)
Angiotensin II antagonists
Anti-angiogenic agents
Antiarrhythmics
Anti-bacterial agents
Antibiotics
    Erythromycin
    Penicillin
    Anti-coagulants
Heparin
Anti-growth factors
Anti-inflammatory agents
    Dexamethasone
    Aspirin
    Hydrocortisone
    Antioxidants
    Anti-platelet agents
Forskolin
Anti-proliferation agents
Anti-rejection agents
    Rapamycin
    Anti-restenosis agents
    Antisense
    Anti-thrombogenic agents
Argatroban
Hirudin
GP IIb/IIIa inhibitors
Anti-virus drugs
Arteriogenesis agents
    acidic fibroblast growth factor (aFGF)
    angiogenin
    angiotropin
    basic fibroblast growth factor (bFGF)
    Bone morphogenic proteins (BMP)
    epidermal growth factor (EGF)
    fibrin
    granulocyte-macrophage colony stimulating factor (GM-CSF)
    hepatocyte growth factor (HGF)
    HIF-1
    Indian hedgehog (Inh)
    insulin growth factor-1 (IGF-1)
    interleukin-8 (IL-8)
    MAC-1
    nicotinamide
    platelet-derived endothelial cell growth factor (PD-ECGF)
    platelet-derived growth factor (PDGF)

TABLE 4-continued

Examples with Some Sub-types of Biological, Pharmaceutical, and other Therapies Deliverable via the Device in Accordance with the Present Invention transforming growth factors alpha & beta (TGF-.alpha., TGF-beta.)
    tumor necrosis factor alpha (TNF-.alpha.)
    vascular endothelial growth factor (VEGF)
    vascular permeability factor (VPF)
Bacteria
Beta blocker
Blood clotting factor
Bone morphogenic proteins (BMP)
Calcium channel blockers
Carcinogens
Cells
    Stem cells
    Bone Marrow
    Blood cells
    Fat Cells
    Muscle Cells
    Umbilical cord cells
    Chemotherapeutic agents
Ceramide
Taxol
Cisplatin
Paclitaxel
Cholesterol reducers
Chondroitin
Clopidegrel (e.g., plavix)
Collagen Inhibitors
Colony stimulating factors
Coumadin
Cytokines prostaglandins
Dentin
Etretinate
Genetic material
Glucosamine
Glycosaminoglycans
GP IIb/IIIa inhibitors
    L-703,081
Granulocyte-macrophage colony stimulating factor (GM-CSF)
Growth factor antagonists or inhibitors
Growth factors
    Autologous Growth Factors
    Bovine derived cytokines
    Cartilage Derived Growth Factor (CDGF)
    Endothelial Cell Growth Factor (ECGF)
    Epidermal growth factor (EGF)
    Fibroblast Growth Factors (FGF)
    Hepatocyte growth factor (HGF)
    Insulin-like Growth Factors (e.g. IGF-I)
    Nerve growth factor (NGF)
    Platelet Derived Growth Factor (PDGF)
    Recombinant NGF (rhNGF)
    Tissue necrosis factor (TNF)
    Tissue derived cytokines
    Transforming growth factors alpha (TGF-alpha)
    Transforming growth factors beta (TGF-beta)
    Vascular Endothelial Growth Factor (VEGF)
    Vascular permeability factor (UPF)
    Acidic fibroblast growth factor (aFGF)
    Basic fibroblast growth factor (bFGF)
    Epidermal growth factor (EGF)
    Hepatocyte growth factor (HGF)
    Insulin growth factor-1 (IGF-1)
    Platelet-derived endothelial cell growth factor (PD-ECGF)
    Tumor necrosis factor alpha (TNF-.alpha.)
Growth hormones
Heparin sulfate proteoglycan
HMC-CoA reductase inhibitors (statins)
Hormones
    Erythropoietin
Immoxidal
Immunosuppressant agents
Inflammatory mediator
Insulin
Interleukins

TABLE 4-continued

Examples with Some Sub-types of Biological, Pharmaceutical, and other Therapies Deliverable via the Device in Accordance with the Present Invention Interlukins
    Interlukin-8 (IL-8)
Lipid lowering agents
Lipo-proteins
Low-molecular weight heparin
Lymphocites
Lysine
MAC-1
Morphogens
    Bone morphogenic proteins (BMPs)
Nitric oxide (NO)
Nucleotides
Peptides
PR39
Proteins
Prostaglandins
Proteoglycans
    Perlecan
Radioactive materials
    Iodine-125
    Iodine-131
    Iridium-192
    Palladium 103
Radio-pharmaceuticals
Secondary Messengers
    Ceramide
Signal Transduction Factors
Signaling Proteins
Somatomedins
Statins
Stem Cells
Steroids
Thrombin
Sulfonyl
Thrombin inhibitor
Thrombolytics
Ticlid
Tyrosine kinase Inhibitors
    ST638
    AG-17
Vasodilator
    Histamine
    Forskolin
    Nitroglycerin
Vitamins
    E
    C
Yeast Also within the inventive concept of the present invention is the placing of a plurality of microstructure materials at strategic locations within the same implant to perform multiple and varied biologic functions. For example, a large osteochondral defect may benefit from hyaluronan velour for the microstructure in the subchondral region intended for osteoneogenesis. The placement of a different microstructure material can be accomplished by various methods, including investing the microstructure material into the regions before they are joined, by investing the device or regions thereof before joining from a first surface with a desired volume of microstructure material less than the total void volume of the macrostructure and then investing from the opposite surface with a volume of a different microstructure material equal to the balance of void volume of the macrostructure.

Except for the critical location at the interface between the cartilage region (or first region, where applicable), the material of the subchondral bone region (or second region, where applicable) is hydrophilic by virtue of being treated with a wetting agent such as set forth in U.S. Pat. No. 4,186,448. For example, beginning at about 200 to 1500 micrometers, but more preferably 500 to 800 micrometers, from the interface surface and extending into the subchondral bone region, the macrostructure polymer of the subchondral bone region may be rendered hydrophobic, such as by treating the entire device or the subchondral bone region with a surfactant and then inactivating the surfactant in the hydrophobic barrier region (i.e., between its interface with the first and second regions or macrostructures), or by not treating the barrier surfaces with a surfactant while the remaining portions are treated.

Likewise, a hydrophobic barrier may be created within a device of simple (i.e. single) or complex (i.e. multiple) internal architectures by other means. For example, a separate fibrillar construct of bioresorbable polymer may be fabricated devoid of surfactant and may be interspersed between two segments of a device whose polymers have been rendered hydrophilic.

For example, in a simple device, such as one used to create cartilage and bone, the bone regeneration region (e.g., alpha-hydroxy-acid) is about 40 to about 90 percent of the apparent volume of the device, with the barrier located between the bone and cartilage regions. It is recognized that the barrier, as described above, may be a material distinct from the first and second regions, or it may exist at or near the surface of one of the regions, prior to the joining of the regions.

Furthermore, the barrier may, in a preferred embodiment, comprise interdigitations of the two joined regions.

In certain applications, it is envisioned that a total fluid or liquid barrier is a necessity, while other applications may have some tolerance or even a need for some liquid through-flow. The type and amount (quantity per application or number of applications) of surfactant can greatly influence the effectiveness of the barrier's inhibition of liquid flow interference. This invention contemplates a barrier that allows no fluid flow, as well as some small amount or retarded flow rate. This entire range of flow being referred to as "inhibited."

Additionally, the term surfactant, as used herein, envisions traditional ionic and stearic treatments, as well as dissimilar material coatings, utilized to alter the host material's response to water and/or certain other liquids. For example, it is envisioned that a hydrophilic coating may be applied to a hydrophobic structure or substrate, thereby rendering the body, or section thereof, hydrophilic, and vice versa.

Alternatively, other surface or chemical modification techniques may be utilized to create a suitable barrier between adjacent regions, or as an intraregional barrier. Such techniques include but are not limited to ion-beam activation, plasma, radio frequency, ultrasound, radiation, and thermal processing.

Water-based fluids, specifically fluid blood, brought to this locale by capillary action through hydrophilic polymer of the subchondral bone region closest to subehondral bone, are prohibited from traveling further toward the cartilage region by a hydrophobic polymer of the subehondral bone region in this vicinity. The interstices of the hydrophobic fibrillar membrane would eventually accommodate cell growth into, and/or migration through, the hydrophobic zone, but the immediate effect of such a membrane would be to prevent passage of water-based fluids across its boundaries.

The hydrophobic barrier is a significant advance and development for devices intended for use in chondroneogenesis, because hyaline cartilage, specifically the articular cartilage of joints, is an avascular tissue and must be protected from intimate contact with sources of high oxygen tension such as blood. When the recipient cartilage tissue defect is prepared to receive the implant, it is necessary to continue the defect into the underlying subchondral bone, called the cancellous bone, to assure that there will be new bone formed beneath the cartilage region which will produce a competent bond with the newly developing cartilage.

The customization of a microenvironment has been disclosed, wherein a three-dimensional architecture may support cell growth. However, the approach was that of a modified cellular structure, not a physical or geometric attribute (Grande, et. al.: A dual gene therapy approach to osteochondral defect repair using a bilayer implant containing BMP-7 and IGF-1 transduced periosteal cells. 47.sup.th Annual Meeting, Orthopaedic Research Society, Feb. 25-28, 2001, San Francisco, Calif.). This technique differs from the present invention as it does not include any subchondral bone sector. Therefore, complete natural bonding between bone and cartilage of sufficient integrity remains problematic.

A similar technique has recently been disclosed, which includes a partition of the microenvironments (Gao J. et. al.: Tissue engineered osteochondral graft using rat marrow-derived mesenchymal stem cells. 47.sup.th Annual Meeting, Orthopaedic Research Society, Feb. 25-28, 2001, San Francisco, Calif.). That construct has two regions glued together with fibrin glue. The regions comprise insoluble hyaluronic acid and tricalcium phosphate. The drawback of this construct is that the barrier is hydrophilic. Additionally, the fibrin glue is quickly bioresorbable and lacks significant adhesive strength. Further, hydrophilic barriers of this construct allow the transport of body fluids and soluble cytokines between regions, which interrupts chondrogenesis and osteogenesis. Barriers which are quickly bioresorbable promote unstable interfaces resulting in mechanical and biological insufficiencies.

Tissue preparation, such as this, engages the rich collateral circulation of subchondral cancellous bone and its associated bone marrow. If the cultured chondrocytes or host cartilage cells come into contact with the fluid blood produced by this source of collateral circulation, they will fail to maintain their chondrocyte phenotype. However, the hydrophobic barrier as may be employed in the present invention described above isolates the cartilage region from contact with whole blood originating in the subchondral bone region. This tissue-specific construct is exemplary, as other regions or tissues and other fluids are contemplated.

It can be appreciated that an anatomically specific device, which may be bioresorbable, according to the teachings of the foregoing inventions having a fabricated macrostructure closely resembling the mature tissues which are to be regenerated by the completed implant, has particular value. Further, integrating one or more of a macrostructure, microstructure, cells cultured in vitro, culture medium and associated growth factors, morphogens, drugs and other therapeutic agents may additionally be beneficial.

According to the teachings of the present invention, the device can be utilized as a transport system for chondrocytes, growth factors, morphogens and other biologically active agents, in treatment of articular cartilage defects. Suitable source tissue is harvested, and the cells are cultured using standard chondrocyte culturing methods, with the specific cell type in the preferred form being articular cartilage chondrocyte. The cartilage defect is surgically prepared by removing diseased or damaged cartilage to create a cartilage and subchondral bone defect, with the defect extending approximately 0.5 cm to 1.0 cm into subchondral cancellous bone. With the device and defect having generally the same shape, the device is inserted into the tissue defect such as by press fitting. A volume of in vitro cell culture suspension is measured out by a microliter syringe which generally matches exactly the void volume of the cartilage region macrostructure invested by the microstructure and is injected onto the outer surface of the tangential zone of the cartilage region and which will ultimately be in contact with synovial fluid. The joint anatomy can then be replaced in proper position and the wound can be closed.

Alternatively, cells or other therapeutic additives may be incorporated during the manufacture of the device, or during the final device preparation (i.e., immediately prior to implant), or as briefly noted above following the implant procedure (e.g., prior to wound closure or as a later therapy, following wound closure).

Although the preferred form relates to the transport and/or in vivo culturing of chondrocytes, it should be noted that the teachings of the present invention, and the useful devices fabricated as a result thereof, are intended to culture and/or transport, and to sustain in life, any cell type having therapeutic value to animals and plants. Various other cell types would be beneficial for tissue other than cartilage or bone, depending on the site and application. The various uses outlined above in text and tabular form are contemplated by this invention.

The term "therapy" has been used in this specification, in various instances. Notwithstanding these various uses, many in combination with other agents (e.g., drug, biologic, biologically active agents, etc.), therapy is not meant to be exclusive of these, but rather to incorporate them. The usage herein is employed to be more descriptive of potential treatment forms, and not limiting as to the definition of the term.

Thus since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalency of the claims are intended to be embraced therein.

What is claimed is:

1. A porous, multi-component device for repair of articular cartilage defects, comprising:
   a. a first region comprising a first component in the form of a microstructure presenting a porous intercommunicating network for cellular attachment, and a second component in the form of a fibrous macrostructure supporting the first component and;
   b. a second region comprising a third component of porous polymer attached to the first and second components.

2. The device of claim 1, wherein said first component comprises acid soluble collagen.

3. The device of claim 1, wherein said second component comprises insoluble collagen.

4. The device of claim 1, wherein said polymer of said third component comprises polymerized alpha-hydroxy acids.

5. The device of claim 1, wherein said third component further comprises at least one ceramic.

6. The device of claim 1, further comprising a fourth component arranged at an interface between said first and second regions.

7. The device of claim 6, wherein said fourth component comprises a film.

8. The device of claim 7, wherein said film is porous.

9. The device of claim 7, wherein said film is hydrophobic.

10. The device of claim 6, wherein said first region comprises a securement complex for the device, said second region comprises a regeneration complex, and said fourth component comprises interdigitations between the first and second regions.

11. The device of claim 1, wherein said device further comprises at least one additive selected from the group consisting of: composite elements, biologics, pharmaceuticals, or therapies.

12. The device of claim 11 wherein said additive is a composite element comprising ceramic.

13. The device of claim 12 wherein the ceramic is selected from at least one of the group consisting of calcium phosphate, calcium sulfate and triealcium phosphate.

14. The device of claim 11 wherein the additive is selected from at least one of the group consisting of antibiotics, anti-coagulants, anti-rejection agents, arteriogenesis agents, cells, chemotherapeutic agents, growth factors, hormones, morphogens or vitamins.

* * * * *